(12) United States Patent
Bilat

(10) Patent No.: US 11,896,059 B2
(45) Date of Patent: Feb. 13, 2024

(54) METHOD OF CONTROLLING HEATING IN AN AEROSOL-GENERATING SYSTEM

(71) Applicant: Philip Morris Products S.A., Neuchatel (CH)

(72) Inventor: Stephane Bilat, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 548 days.

(21) Appl. No.: 17/261,209

(22) PCT Filed: Jul. 19, 2019

(86) PCT No.: PCT/EP2019/069600
§ 371 (c)(1),
(2) Date: Jan. 19, 2021

(87) PCT Pub. No.: WO2020/020796
PCT Pub. Date: Jan. 30, 2020

(65) Prior Publication Data
US 2021/0161214 A1 Jun. 3, 2021

(30) Foreign Application Priority Data
Jul. 25, 2018 (EP) ..................................... 18185605

(51) Int. Cl.
*A24F 40/57* (2020.01)
*A24F 40/53* (2020.01)
(Continued)

(52) U.S. Cl.
CPC .............. *A24F 40/57* (2020.01); *A24F 40/53* (2020.01); *H05B 1/0297* (2013.01); *A24F 40/10* (2020.01); *A24F 40/46* (2020.01)

(58) Field of Classification Search
CPC .......... A24F 40/57; A24F 40/53; A24F 40/10; A24F 40/46; H05B 1/0297
(Continued)

(56) References Cited

U.S. PATENT DOCUMENTS

2006/0047368 A1 3/2006 Maharajh et al.
2014/0014126 A1 1/2014 Peleg et al.
(Continued)

FOREIGN PATENT DOCUMENTS

CN 103974638 A 8/2014
JP 2006-214885 A 8/2006
(Continued)

OTHER PUBLICATIONS

International Search Report and Written Opinion dated Oct. 25, 2019 in PCT/EP2019/069600 filed Jul. 19, 2019.
(Continued)

*Primary Examiner* — Gary F Paumen
(74) *Attorney, Agent, or Firm* — Oblon, McClelland, Maier & Neustadt, L.L.P.

(57) ABSTRACT

A method of controlling heating in an aerosol-generating system including a heater is provided, the method including: a first control step in which a predetermined power is provided to the heater and a resistance of the heater is determined, the determined resistance being indicative of a temperature of the heater; monitoring for a predetermined condition, and upon detection of the predetermined condition, recording a resistance of the heater; determining a target resistance corresponding to a target temperature of the heater based on the recorded resistance; and a second control step in which the predetermined power provided to the heater is controllably adapted to drive the resistance of the heater towards the target resistance such that the heater is driven towards the target temperature corresponding to the (Continued)

target resistance. An aerosol-generating system and a controller for an aerosol-generating system are also provided.

20 Claims, 7 Drawing Sheets

(51) Int. Cl.
*H05B 1/02* (2006.01)
*A24F 40/10* (2020.01)
*A24F 40/46* (2020.01)

(58) Field of Classification Search
USPC .......................................................... 131/328
See application file for complete search history.

(56) References Cited

U.S. PATENT DOCUMENTS

| | | | | |
|---|---|---|---|---|
| 2014/0345606 | A1* | 11/2014 | Talon | A61M 16/0003 |
| | | | | 128/203.14 |
| 2015/0230521 | A1* | 8/2015 | Talon | A24F 40/50 |
| | | | | 131/328 |
| 2015/0237916 | A1* | 8/2015 | Farine | A24F 40/53 |
| | | | | 219/492 |
| 2015/0359263 | A1 | 12/2015 | Bellinger | |
| 2017/0340010 | A1* | 11/2017 | Bilat | F22B 1/284 |
| 2018/0020735 | A1* | 1/2018 | Bilat | H05B 3/44 |
| | | | | 131/328 |
| 2018/0043114 | A1 | 2/2018 | Bowen et al. | |
| 2018/0077967 | A1 | 3/2018 | Hatton et al. | |
| 2018/0084608 | A1* | 3/2018 | Bernauer | H05B 1/0291 |
| 2018/0093054 | A1 | 4/2018 | Bowen et al. | |
| 2019/0069599 | A1 | 3/2019 | Monsees et al. | |

FOREIGN PATENT DOCUMENTS

| | | |
|---|---|---|
| JP | 2009-164472 A | 7/2009 |
| JP | 2015-524260 A | 8/2015 |
| JP | 3216733 U | 6/2018 |
| WO | WO 2013/098397 A2 | 7/2013 |
| WO | WO 2017/147560 A1 | 8/2017 |
| WO | WO 2017/205692 A1 | 11/2017 |

OTHER PUBLICATIONS

Japanese Office Action dated Jun. 26, 2023 in Japanese Patent Application No. 2021-503557 (with English Abstract), 5 pages.
European Office Action dated Feb. 25, 2022 in European Patent Application No. 19 742 743.8, 73 pages.
Chinese Office Action and Search Report dated Oct. 17, 2023 issued in Chinese Patent Application No. 201980044524.1 filed on Jul. 19, 2019, with English Translation, total 9 pages.

* cited by examiner

METHOD OF CONTROLLING HEATING IN AN AEROSOL-GENERATING SYSTEM

The present invention relates to a method of controlling heating in an aerosol-generating system comprising a heater and also to such an aerosol-generating system. In particular, the invention relates to handheld electrically-operated aerosol-generating systems which vaporise an aerosol-forming substrate by heating to generate an aerosol.

Electrically operated aerosol-generating systems are known. Such systems typically consist of a device portion having a battery and control electronics, an aerosol-forming substrate, an electric heater comprising at least one resistive heating element arranged to heat the aerosol-forming substrate and a mouthpiece. In some systems, the aerosol-forming substrate comprises a liquid and an elongate wick is used to convey the liquid aerosol-forming substrate to the heater. The heater typically comprises a coil of resistive heating wire which is wound around the elongate wick. The heater, wick and liquid aerosol-forming substrate are often contained within a cartridge which can be attached to or received within the device portion. When a user activates the device, an electric current passes through the heater causing resistive heating which vaporises the liquid in the wick. By inhaling through or puffing on the mouthpiece, air is drawn through the system and entrains the vapour, which subsequently cools to form an aerosol. Aerosol laden air leaves the system via the mouthpiece and enters a user's mouth.

As used herein, the term 'aerosol-generating substrate' relates to a substrate capable of releasing volatile compounds that can form an aerosol. Such volatile compounds may be released by heating the aerosol-forming substrate. An aerosol-forming substrate may conveniently be part of an aerosol-generating article or system.

It is generally desirable for aerosol-generating systems to be able to produce aerosol which is consistent over time. This is particularly the case when the aerosol is for human consumption because variations in the aerosol can detract from the user's experience and extreme variations can be potentially hazardous. It is also generally desirable for aerosol-generating systems to produce aerosol as efficiently as possible in terms of the amount of energy required to generate the aerosol. However, this can be difficult to achieve due to variations in the manufacturing process of the systems, variations in the properties of the aerosol-forming substrates used in such systems and the different operating conditions under which such systems are used.

In aerosol-generating systems which use a liquid aerosol-forming substrate, it is also desirable to be able to detect and avoid a "dry heating" situation, i.e. a situation in which the heater is heated with insufficient liquid aerosol-forming substrate being present. This situation is also known as a "dry puff" and can result in overheating and, potentially, thermal decomposition of the liquid aerosol-forming substrate, which can produce undesirable by-products such as formaldehyde.

In order to produce a consistent aerosol, it may be desirable to control or regulate the temperature of the heater used to heat the aerosol-forming substrate.

It is an object of the present invention to provide an aerosol-generating system that provides an aerosol that is more consistent in its properties during heating of the aerosol-forming substrate. It is a further object of the present invention to provide an aerosol-generating system that heats an aerosol-forming substrate more efficiently and reduces the likelihood of a dry puff.

According to a first aspect of the present invention, there is provided a method of controlling heating in an aerosol-generating system comprising a heater, the method comprising: a first control step in which a predetermined power is provided to the heater and the resistance of the heater is determined, wherein the determined resistance is indicative of the heater's temperature; monitoring for a predetermined condition and upon detection of the predetermined condition, recording the resistance of the heater; determining a target resistance corresponding to a target temperature of the heater based on the recorded resistance; and a second control step in which the power provided to the heater is controllably adapted to drive the resistance of the heater towards the target resistance such that the heater is driven towards a target temperature corresponding to the target resistance.

One way of controlling or regulating the temperature of a heater is power regulation. In a power regulated system, a predetermined or constant power is provided to the heater and the resistance of the heater is monitored. Since the relationship between the electrical resistance of the heater and the temperature of the heater is generally known or can be determined, the resistance of the heater is able to provide an indication of the heater's temperature. For example, the electrical resistance of the heater may be known to be proportional to the temperature of the heater, in which case there will be a substantially linear relationship between resistance and temperature.

Upon provision of the predetermined or constant power, the temperature of the heater will initially increase rapidly, e.g. within approximately 0.3 seconds, towards a target temperature. Generally, the power is selected such that the temperature of the heater starts to stabilise in the region of the target temperature. However, less power is generally required to maintain the temperature of the heater at the target temperature than is required to heat it up. Consequently, if a constant power continues to be delivered to the heater, the temperature of the heater will continue to increase for a period of time beyond the target temperature but at a lower rate. By monitoring resistance, the power to the heater can be reduced or stopped if the resistance becomes too high, i.e. if the temperature of the heater increases beyond the target temperature. However, there is a tendency for the temperature of the heater to "overshoot" the target temperature in a power regulated system. This can be undesirable because it can lead to increased aerosol generation and hence variability in aerosol delivery during a user inhalation. Furthermore, overshooting the target temperature means that energy is wasted, which adversely affects the efficiency of the device.

Another way of controlling or regulating the temperature of a heater is resistance regulation. In a resistance regulated system, a target resistance indicative of a target temperature is set and the power supplied to the heater is adapted such that the resistance of the heater is driven towards or maintained at or in the region of the target resistance. However, regulating temperature using resistance regulation can be problematic because of difficulties in calculating the target resistance due to various factors which affect the resistance of the heater such as manufacturing variations, variability of contact resistance, varying properties of the aerosol-generating substrate, different ambient temperatures and differing geometries, materials and resistances of various heaters.

The method of the first aspect of the invention uses two control steps to control heating in an aerosol-generating system; a first control step that is based on power regulation and a second control step which is based on resistance regulation. This results in a hybrid method of regulation which means that the advantages of both types of regulation can be exploited whilst the disadvantages of each type can be reduced. Such a hybrid method provides a number of benefits, as follows.

A first control step based on power regulation only requires a constant power to be provided to the heater and for the resistance of the heater to be determined. There is no need to adapt the power during this control step and therefore it is relatively straightforward to control and uses less control resources compared to resistance regulation. This is beneficial during the initial stages of a heating cycle, i.e. whilst the heater is simply heating up, because there is less need to regulate the temperature during this time.

Upon detection of a predetermined condition the resistance is recorded and the recorded resistance can be used to determine a target resistance based on the recorded resistance. Since the target resistance is simply based on the resistance of the heater recorded at the time of detecting the predetermined condition, the target resistance can be determined independently of various factors which may otherwise affect the resistance of the heater such as manufacturing variations, variability of contact resistance, varying properties of the aerosol-generating substrate, different ambient temperatures and differing geometries, materials and resistances of various heaters.

Following determination of the target resistance, a second control step based on resistance regulation can then be used in which the power provided to the heater is controllably adapted to drive the resistance of the heater towards the target resistance such that the heater is driven towards a target temperature corresponding to the target resistance. This reduces the likelihood of the temperature of the heater overshooting the target temperature. Consequently, the consistency or uniformity of the properties of the generated aerosol are improved both during an inhalation and for subsequent inhalations. For example, the volume of aerosol delivered can be made more consistent as can the constituents contained within the aerosol. This results in an overall improved user experience. Furthermore, by reducing temperature overshoots, less energy is wasted and the efficiency of the system is improved.

As used herein, the term 'target resistance' refers to an electrical resistance of the heater which is determined based on the resistance of the heater recorded upon detection of the predetermined condition. As discussed above, since the relationship between the electrical resistance of the heater and the temperature of the heater is generally known or can be determined, the resistance of the heater is able to provide an indication of the heater's temperature. Therefore, the target resistance has a corresponding target temperature and vice versa.

As used herein, the term 'target temperature' refers to a temperature or temperature range corresponding to the target resistance. The target temperature is sufficient to generate an aerosol from the aerosol-forming substrate but is below a temperature at which thermal decomposition of the aerosol-forming substrate occurs or undesirable by-products are produced.

The method may switch from the first control step to the second control step upon detection of the predetermined condition. This allows for a rapid response to the predetermined condition.

As used herein, the term 'predetermined condition' refers to a condition or criteria which indicates that the resistance of the heater is at or near the target resistance. The condition may be known or determined in advance of carrying out the method. As discussed above, when power is provided to the heater, the temperature and hence the resistance of the heater initially increases rapidly before starting to stabilise around the target temperature. The point at which the resistance starts to stabilise can be monitored and various points within the stabilisation set as the predetermined condition.

The predetermined condition may be selected from one or more different conditions, as follows.

As one example, the predetermined condition may be an elapsed time from the start of a user inhalation. The time taken for the resistance to stabilise at or near the target temperature may be known or can be determined and this time can be used as the predetermined condition.

As another example, the predetermined condition may be a derivative of resistance which is less than a predetermined threshold. As used herein, the term 'derivative of resistance' refers to a measure of the sensitivity to change of resistance with respect to a change in another variable. For example, the derivative may be the rate of change of resistance with time, e.g. the gradient of a resistance versus time curve, or the derivative may be an absolute change in resistance within a sampling time. As resistance starts to stabilise around the target temperature, the rate of change of resistance with time starts to decrease. The predetermined condition may be a certain value for the rate of change of resistance and the method may monitor when the rate of change of resistance drops below this value.

As yet another example, the predetermined condition may be a derivative of resistance which is equal to zero. When the temperature of the heater has reached the highest temperature it will reach for a given power, the rate of change of temperature and hence the rate of change of resistance will become zero. This zero rate of change of resistance may be used as the predetermined condition.

In addition, the predetermined condition can be any suitable criteria based on resistance and/or time.

The first control step and the second control step may be performed during a user inhalation, and optionally during each user inhalation or puff. This allows a target resistance to be set and effectively optimised for each inhalation. This is particularly useful if the target resistance is likely to change between puffs, for example, if aerosol-forming substrate is becoming depleted or the ambient operating conditions are changing quickly.

As used herein, the terms 'inhalation' and 'puff' are used interchangeably and are intended to mean the action of a user drawing on an end of the system to draw aerosol from the system.

The first control step and the second control step may be performed during a first user inhalation, and a second and subsequent user inhalations may use only the second control step. This allows a target resistance to be set by the first user inhalation and to be used in all subsequent inhalations such that a consistent aerosol will be produced across all subsequent inhalations in a particular user session. If desired, the temperature of the heater can be increased more quickly to the target temperature than with the first control step, which is based on power regulation, because the second control step is not limited by having to provide constant power. In other words, the power can be increased beyond the constant power of the first control step, if the system requires, in order to drive the temperature of the heater towards the target temperature more quickly.

The target resistance may be determined following a plurality of initial user inhalations. Optionally, only the first control step and the step of monitoring and detecting a predetermined condition and recording the resistance may be performed during a plurality of initial user inhalations.

For this option, switching to the second control mode will occur between inhalations and not during the inhalation.

The target resistance may be determined based on an average of the recorded resistances from the plurality of initial user inhalations. A target resistance based on an average of the recorded resistances from the plurality of initial user inhalations may allow variation in the initial recorded resistances to be accounted for or evened out, for example, during the initial start-up of an aerosol-generating system before the system has thermally stabilised or if ambient operating conditions change suddenly upon start-up, for example, by the user moving from outdoors to indoors.

User inhalations following the plurality of initial user inhalations may use only the second control step and the target resistance may be based on the average of the recorded resistances from the plurality of initial user inhalations. This may provide for consistent aerosol production for subsequent inhalations in a particular user session. If desired, the temperature of the heater can be increased more quickly to the target temperature than with the first control step, which is based on power regulation, because the second control step is not limited by having to provide constant power.

According to a second aspect of the present invention, there is provided an aerosol-generating system comprising: a heater; a power supply; and a controller; wherein the controller is configured to: provide a predetermined power to the heater and determine the resistance of the heater in a first control mode, wherein the determined resistance is indicative of the heater's temperature; monitor for a predetermined condition and upon detection of the predetermined condition, record the resistance of the heater; determine a target resistance corresponding to a target temperature of the heater based on the recorded resistance; and controllably adapt the power provided to the heater to drive the resistance of the heater towards the target resistance in a second control mode such that the heater is driven towards a target temperature corresponding to the target resistance.

The system of the second aspect of the invention uses two control modes to control heating in an aerosol-generating system; a first control mode that is based on power regulation and a second control mode which is based on resistance regulation. The first and second control modes correspond to the first and second control steps of the method of the first aspect of the invention. Consequently, the system is configured with hybrid temperature regulation which means that the advantages of both types of regulation can be exploited whilst the disadvantages of each type can be reduced. Such a hybrid regulation provides a number of benefits, which are discussed above under the first aspect of the invention and, for conciseness, are not repeated here.

The controller may be configured to switch from the first control mode to the second control mode upon detection of the predetermined condition. This allows for a rapid response to the predetermined condition.

The predetermined condition may be selected from one or more of the following: i) an elapsed time from the start of a user inhalation; ii) a derivative of resistance being less than a predetermined threshold; and iii) a derivative of resistance being equal to zero. Each of these predetermined conditions are the same as the predetermined conditions for the first aspect of the invention and are discussed above. For conciseness, that discussion is not repeated here. In addition, the predetermined condition can be any suitable criteria based on resistance and/or time.

The first control mode and the second control mode may be used during a user inhalation, and optionally during each user inhalation. This allows a target resistance to be set and effectively optimised for each inhalation. This is particularly useful if the target resistance is likely to change between puffs, for example, if aerosol-forming substrate is becoming depleted or the ambient operating conditions are changing quickly.

The first control mode and the second control mode may be used during a first user inhalation, and a second and subsequent user inhalations may use only the second control mode. This allows a target resistance to be set by the first user inhalation and to be used in all subsequent inhalations such that a consistent aerosol will be produced across all subsequent inhalations in a particular user session. If desired, the temperature of the heater can be increased more quickly to the target temperature than with the first control mode, which is based on power regulation, because the second control mode is not limited by having to provide constant power. In other words, the power can be increased beyond the constant power of the first control mode if the system requires in order to drive the temperature of the heater towards the target temperature more quickly.

The target resistance may be determined following a plurality of initial user inhalations. Optionally, only the first control mode and the monitoring and detecting of a predetermined condition and recording the resistance may be used during a plurality of initial user inhalations. For this option, switching to the second control mode will occur between inhalations and not during the inhalation.

The target resistance may be determined based on an average of the recorded resistances from the plurality of initial user inhalations. A target resistance based on an average of the recorded resistances from the plurality of initial user inhalations may allow variation in the determined target resistance to be accounted for or evened out, for example, during the initial start-up of an aerosol-generating system before the system has thermally stabilised or if ambient operating conditions change suddenly upon start-up, for example, by the user moving from outdoors to indoors.

User inhalations following the plurality of initial user inhalations may use only the second control mode and the target resistance may be based on the average of the recorded resistances from the plurality of initial user inhalations. This may provide for consistent aerosol production for subsequent inhalations in a particular user session. If desired, the temperature of the heater can be increased more quickly to the target temperature than with the first control mode, which is based on power regulation, because the second control mode is not limited by having to provide constant power.

In both the first and second aspects of the invention, the heater may comprise an electrically resistive heating element. The heater may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum platinum, gold and silver. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required.

In both the first and second aspects of the invention, the heater may comprise an internal heating element or an external heating element, or both internal and external heating elements, where "internal" and "external" refer to a position relative to the aerosol-forming substrate. An internal heating element may take any suitable form. For example, an internal heating element may take the form of a heating blade. Alternatively, the internal heater may take the form of a casing or substrate having different electro-conductive portions, or an electrically resistive metallic tube. Alternatively, the internal heating element may be one or more heating needles or rods that run through the centre of the aerosol-forming substrate. Other alternatives include a heating wire or filament, for example a Ni—Cr (Nickel-Chromium), platinum, tungsten or alloy wire or a heating plate. Optionally, the internal heating element may be deposited in or on a rigid carrier material. In one such embodiment, the electrically resistive heating element may be formed using a metal having a defined relationship between temperature and resistivity. In such an exemplary device, the metal may be formed as a track on a suitable insulating material, such as a ceramic material, and then sandwiched in another insulating material, such as a glass. Heaters formed in this manner may be used to both heat and monitor the temperature of the heating elements during operation.

The heater may comprise a fluid permeable heating element. The fluid permeable heating element may be substantially flat and may comprise electrically conductive filaments. The electrically conductive filaments may lie in a single plane. In other embodiments, the substantially flat heating element may be curved along one or more dimensions, for example forming a dome shape or bridge shape.

The electrically conductive filaments may define interstices between the filaments and the interstices may have a width of between 10 μm and 100 μm. The filaments may give rise to capillary action in the interstices, so that in use, a liquid aerosol-forming substrate is drawn into the interstices, increasing the contact area between the heating element and the liquid.

The electrically conductive filaments may form a mesh of size between 160 and 600 mesh US (+/−10%) (i.e. between 160 and 600 filaments per inch (+/−10%)). The width of the interstices is preferably between 75 μm and 25 μm. The percentage of open area of the mesh, which is the ratio of the area of the interstices to the total area of the mesh is preferably between 25 and 56%. The mesh may be formed using different types of weave or lattice structures. Alternatively, the electrically conductive filaments consist of an array of filaments arranged parallel to one another.

The electrically conductive filaments may have a diameter of between 10 μm and 100 μm, preferably between 8 μm and 50 μm, and more preferably between 8 μm and 39 μm. The filaments may have a round cross section or may have a flattened cross-section. The heater filaments may be formed by etching a sheet material, such as a foil. If the heater assembly comprises a mesh or fabric of filaments, the filaments may be individually formed and knitted together.

The area of the fluid permeable heating element may be, for example, less than or equal to 50 square millimetres, preferably less than or equal to 25 square millimetres, more preferably approximately 15 square millimetres.

The electrical resistance of the mesh, array or fabric of electrically conductive filaments of the heating element may be between 0.3 Ohms and 4 Ohms. Preferably, the electrical resistance is equal or greater than 0.5 Ohms. More preferably, the electrical resistance of the mesh, array or fabric of electrically conductive filaments is between 0.6 Ohms and 0.8 Ohms.

The aerosol-forming substrate may be a liquid aerosol-forming substrate. If a liquid aerosol-forming substrate is provided, the aerosol-generating system preferably comprises means for retaining the liquid. For example, the liquid aerosol-forming substrate may be retained in a liquid storage portion or a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic.

If a liquid aerosol-forming substrate is provided, both the first and second aspects of the invention may be configured to detect a dry puff, for example, by detecting when the recorded resistance increases above a threshold value or by detecting when the power required to maintain the heater at the target resistance decreases below a threshold value.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former. Examples of suitable aerosol formers are glycerine and propylene glycol.

The aerosol-generating system may comprise a housing having a mouthpiece portion and a body portion. The body portion may comprise an electric power supply, for example, a rechargeable lithium ion battery, control circuitry having a controller, for example, a microcontroller and a user interface for activating the heater, for example, a puff detection device or a push button. The mouthpiece portion may comprise a liquid storage portion, for example, a cartridge containing a liquid aerosol-generating substrate. The cartridge may comprise a capillary material for conveying liquid aerosol-forming substrate to the heater. The cartridge may also comprise the heater.

The control circuitry may be arranged to provide power to the heating element as a series of electrical voltage pulses. The power provided to the heating element may then be adjusted by adjusting the duty cycle of the voltage pulses. The duty cycle may be adjusted by altering the pulse width, or the frequency of the pulses or both. Alternatively, the circuitry may be arranged to provide power to the heating element as a continuous DC signal. A proportional-integral-derivative (PID) control loop may be used to drive the resistance of the heater towards a target resistance.

According to a third aspect of the present invention, there is provided a controller for an aerosol-generating system, the controller being configured to perform any of the methods described above.

According to a fourth aspect of the present invention, there is provided a computer program which, when run on a programmable controller for an aerosol-generating system, causes the programmable controller to perform any of the methods described above.

Features described in relation to one aspect may equally be applied to other aspects of the invention.

Embodiments of the invention will now be described, by way of example only, with reference to the accompanying drawings, in which.

Figure 1:
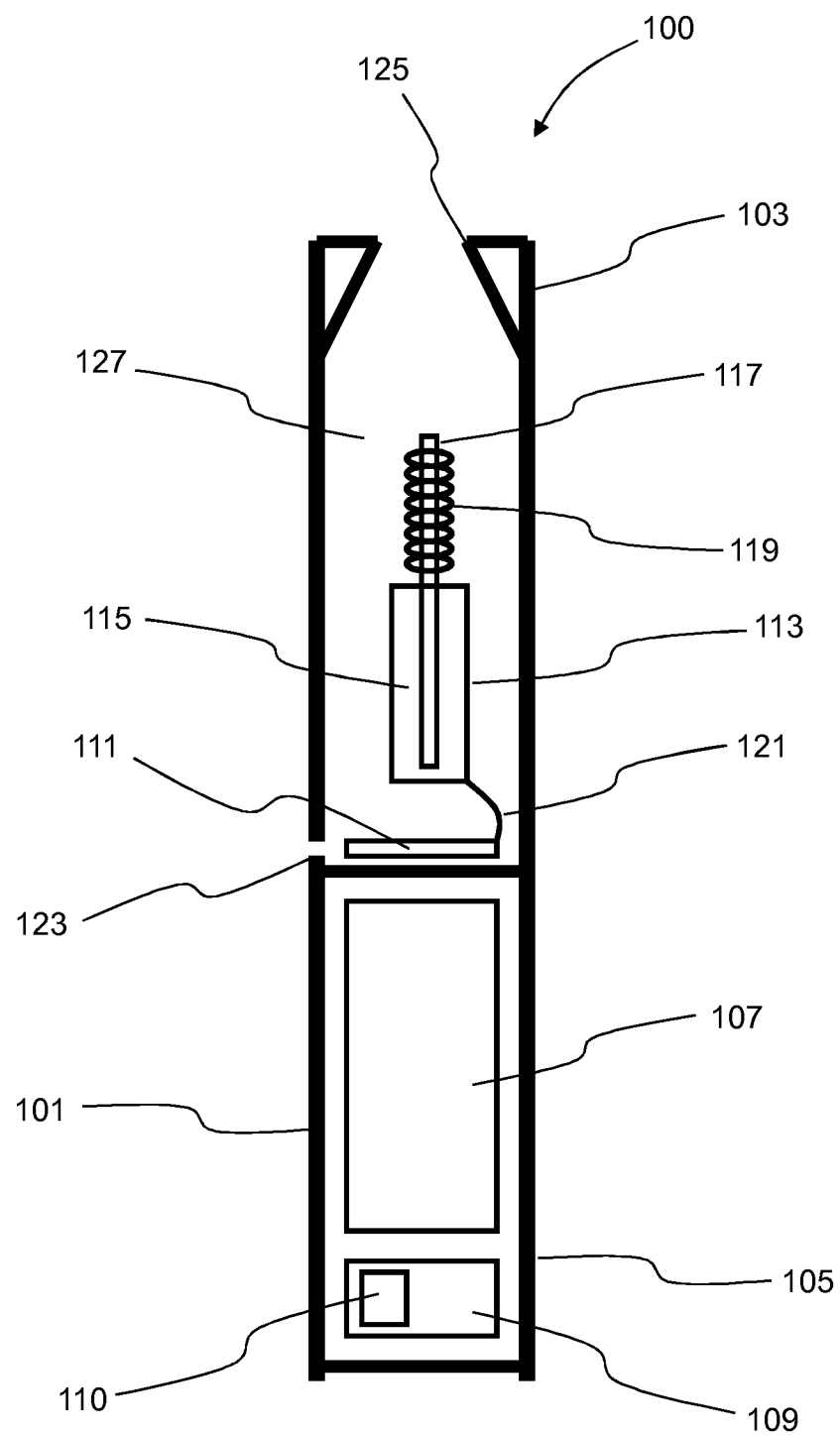
FIG. 1 is a schematic illustration of an aerosol-generating system in accordance with an embodiment of the invention.

FIG. 1 is a schematic illustration of an aerosol-generating system. The system 100 comprises a housing 101 having a mouthpiece portion 103 and a body portion 105. In the body portion 105, there is provided an electric power supply 107, for example, a rechargeable lithium ion battery, control circuitry 109 having a controller 110, for example, a microcontroller and a puff detection device 111. In the mouthpiece portion 103, there is provided a liquid storage portion 113, for example, a cartridge containing a liquid aerosol-generating substrate 115, a wick 117 formed of a capillary material and a heater 119 comprising at least one heating element. One end of the wick 117 extends into the cartridge 113 and the other end of the wick 117 is surrounded by the heater 119. The heater 119 is connected to the puff detection device 111 via connections 121 which in turn is connected to the control circuitry 109 by further connections (not shown). The housing 101 also includes an air inlet 123 in the region of the puff detection device 111, an air outlet 125 which exits the mouthpiece portion 103 and an aerosol-forming chamber 127 surrounding the heater 119.

Liquid aerosol-forming substrate 115 is transferred or conveyed by the wick 117 via capillary action from the cartridge 113 to the end of the wick surrounded by the heater 119. In use, a user inhales through or puffs on the mouthpiece portion 103, ambient air is drawn through air inlet 123. The inhalation or puff is detected or sensed by the puff detection device 111, which activates the heater 119. The battery 107 supplies energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. The supersaturated vapour created is mixed with and carried in the airflow from the air inlet 123 and condenses in the aerosol-forming chamber 127 to form an inhalable aerosol, which is carried towards the outlet 125 and into the mouth of the user.

The controller 110 is programmable and has embedded software or firmware to control the power supplied to the heater 119 in order to regulate its temperature. This, in turn, affects the temperature profile of the heater which will affect the amount of aerosol produced. The controller 110 provides power to the heater 119 by pulse width modulation (PWM) which uses a series of pulses of electrical voltage to transmit power. The power provided to the heater can be varied by varying the duty cycle of the pulses at constant frequency. The duty cycle is the ratio of the time that the power is switched on to the time the power is switched off. In other words, the ratio of the width of the voltage pulses to the time between the voltage pulses. For example, a low duty cycle of 5% will provide much less power than a duty cycle of 95%.

Figure 2:
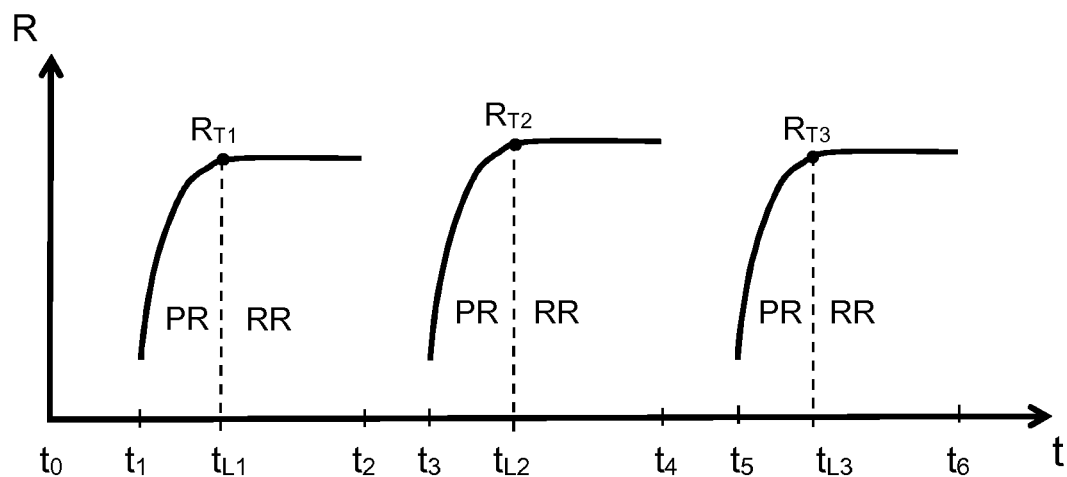
FIG. 2 is a schematic illustration of a temperature profile of a heater of an aerosol-generating system obtained by a method in accordance with an embodiment of the present invention.

FIG. 2 shows a graph of resistance R versus time t and the temperature profile of a heater of an aerosol-generating system which is heated by a method in accordance with an embodiment of the present invention. In particular, FIG. 2 shows the first three inhalations or puffs of a user session in which all three inhalations are controlled by hybrid regulation, i.e. a combination of power regulation and resistance regulation.

The system is enabled at time $t_0$, for example, by the user turning the system on. The user starts to take a first inhalation or puff at time $t_1$, which activates the heater. The heater is initially controlled by a first control step or mode based on power regulation (denoted by PR in the figures) in which a constant predetermined power corresponding to predetermined duty cycle is provided to the heater. The predetermined power may be relatively high, for example, an 80% to 95% duty cycle, in order to raise the temperature of the heater rapidly. The provision of the predetermined power causes the temperature of the heater to increase and the resistance of the heater is determined at regular intervals to provide an indication of the heater's temperature. The predetermined power is provided to the heater until a predetermined condition is detected at time $t_{L1}$, at which point the resistance is locked or recorded and a target resistance $R_{T1}$ is determined based on the recorded resistance. In general, the target resistance will be the same as the recorded resistance, although it is also possible for the target resistance to be different from the recorded resistance, for example, a function of the recorded resistance or to include a known error correction, depending on the requirements of the system. Using this method, the target resistance is determined independently of any variability in the resistance of the heater or characteristics of the system. The target resistance corresponds to a target temperature to which the heater should be heated.

In the example of FIG. 2, the predetermined condition is a point at which the rate of change of resistance drops below a certain threshold value, i.e. a point at which the gradient of the temperature profile reduces to a predetermined value. In particular, in FIG. 2, the predetermined condition is the point at which the gradient of the temperature profile approaches zero.

At time $t_{L1}$, control of the heater switches to a second control step or mode based on resistance regulation (denoted by RR in the figures) in which the power provided to the heater is controllably adapted to drive the resistance of the heater towards the target resistance $R_{T1}$ such that the heater is driven towards a target temperature corresponding to the target resistance $R_{T1}$. The second control step or mode uses PID control to regulate the resistance. The PID control is integrated into the software programmed into the controller. To regulate the resistance, the resistance of the heater is determined and an error between the determined resistance and the target resistance $R_{T1}$ is calculated. The duty cycle of the power is then adjusted using PID control to correct the error and drive the heater toward the target resistance. The resistance is determined at a frequency chosen to match the frequency at which the duty cycle is controlled, and may be determined once every 100 ms or more frequently, as required.

Following the switch to the second control step or mode based on resistance regulation at time $t_{L1}$, the resistance is maintained substantially constantly at the target resistance $R_{T1}$ until the user stops their first inhalation or puff at time $t_2$.

In the example of FIG. 2, similar hybrid regulation to that described above is used in each subsequent inhalation or puff. The user initiates second and third inhalations at times $t_3$ and $t_5$ respectively and corresponding target resistances $R_{T2}$ and $R_{T3}$ are determined at times $t_{L2}$ and $t_{L3}$ respectively. Each of the three inhalations in FIG. 2 has its own target resistance, i.e. $R_{T1}$, $R_{T2}$ and $R_{T3}$ respectively. The target resistances are substantially similar but differ slightly to account for slightly different conditions in each inhalation such that the target resistances $R_{T1}$, $R_{T2}$ and $R_{T3}$ are optimised for each inhalation.

Figure 3:
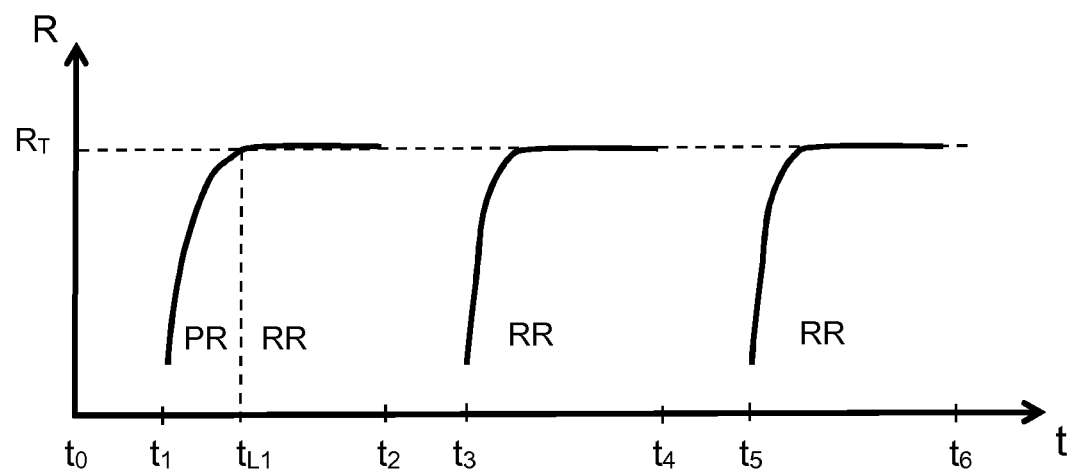
FIG. 3 is a schematic illustration of a temperature profile of a heater of an aerosol-generating system obtained by a method in accordance with another embodiment of the present invention.

FIG. 3 shows a graph of resistance R versus time t and the temperature profile of a heater of an aerosol-generating system which is heated by a method in accordance with another embodiment of the present invention. In particular, FIG. 3 shows the first three inhalations or puffs of a user session in which only the first inhalation is regulated by hybrid regulation and the second and subsequent inhalations are regulated using resistance regulation only.

In FIG. 3, the system is enabled at time to and the user starts to take a first inhalation or puff at time $t_1$, which activates the heater. The first inhalation of FIG. 3 is regulated in the same way as the inhalations in FIG. 2. During the first inhalation, the heater is initially controlled by a first control step or mode based on power regulation. Upon detection of a predetermined condition at time $t_{L1}$, a resistance is recorded and a target resistance $R_T$ is determined based on the recorded resistance. At which point, control of the heater switches to a second control step or mode based on resistance regulation, which is used for the remainder of the inhalation until the inhalation terminates at time $t_2$.

The second and third inhalations in FIG. 3 are initiated at times $t_3$ and $t_5$ respectively, at which times the heater is again activated but is controlled by a second control step only based on resistance regulation until the inhalations terminate at times $t_4$ and $t_6$ respectively. The second and subsequent inhalations are therefore regulated based on the target resistance $R_T$ of the first inhalation. This provides consistent aerosol generation across all inhalations. In addition, the heater can be brought to the target temperature corresponding to the target resistance $R_T$ more quickly, if required, because the second control step or mode is not limited to providing a constant predetermined power but can provide power up to a 100% duty cycle if needed to bring the temperature of the heater to the target temperature as quickly as possible. As can be seen in FIG. 3, the temperature profiles of the second and third inhalations have steeper gradients compared to the first inhalation, which indicates a faster rate of temperature change. The second control step or mode used for regulating the second and third inhalations uses PID control to regulate the resistance, which is integrated into the software programmed into the controller.

Figure 4:
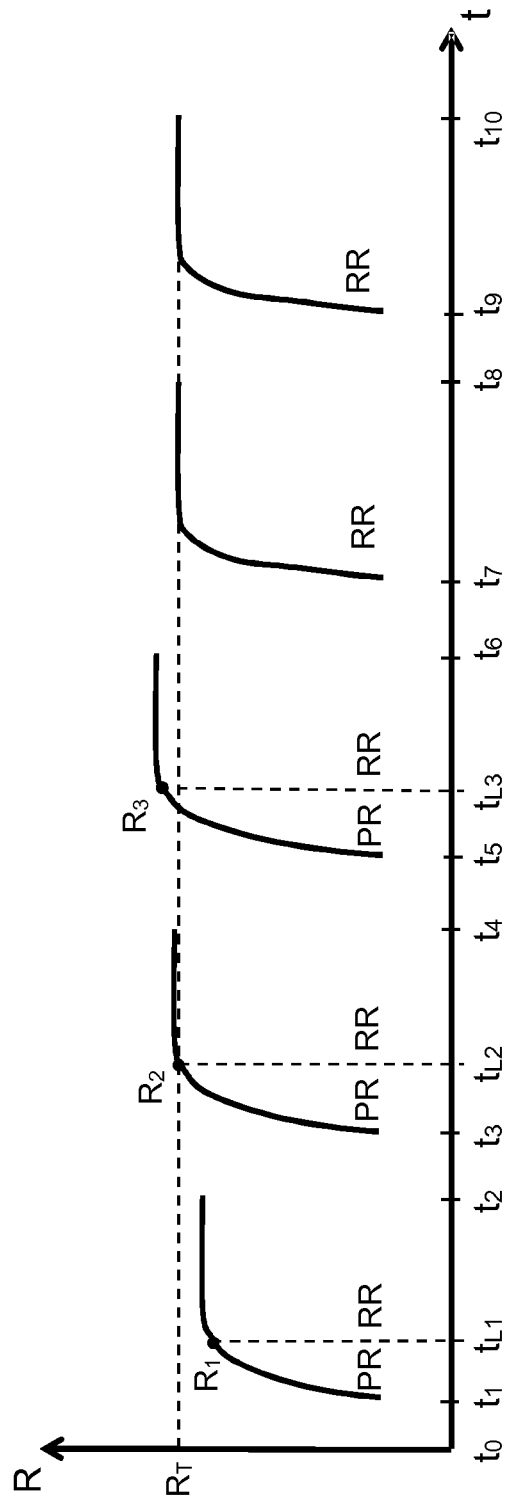
FIG. 4 is a schematic illustration of a temperature profile of a heater of an aerosol-generating system obtained by a method in accordance with another embodiment of the present invention.

FIG. 4 shows a graph of resistance R versus time t and the temperature profile of a heater of an aerosol-generating system which is heated by a method in accordance with another embodiment of the present invention. In particular, FIG. 4 shows the first five inhalations or puffs of a user session in which the first three inhalations are regulated by hybrid regulation and the fourth and subsequent inhalations are regulated using resistance regulation only.

In FIG. 4, the system is enabled at time $t_0$ and the user takes the first inhalation or puff at time $t_1$, at which time the heater is activated. The first inhalation of FIG. 4 is regulated in the same way as the inhalations in FIG. 2. During the first inhalation, the heater is initially controlled by a first control step or mode based on power regulation, in which a constant predetermined power corresponding to predetermined duty cycle is provided to the heater. The predetermined power is provided to the heater until a predetermined condition is detected at time $t_{L1}$, at which point the resistance $R_1$ is locked or recorded. The predetermined condition in the example of FIG. 4 is again the point at which the gradient of the temperature profile approaches zero. A target resistance is not determined at this point. Instead, the method will firstly monitor one or more further inhalations or puffs before determining a target resistance.

At time $t_{L1}$ in FIG. 4, control of the heater switches to a second control step or mode based on resistance regulation in which the power provided to the heater is controllably adapted to drive the resistance of the heater towards the recorded resistance $R_1$ such that the heater is driven towards a temperature corresponding to the recorded resistance $R_1$. The second control step or mode uses PID control integrated into the software programmed into the controller to regulate the resistance.

Following the switch to the second control step or mode based on resistance regulation at time $t_{L1}$ in FIG. 4, the resistance is maintained substantially constantly at the recorded resistance $R_1$ until the user stops their first inhalation or puff at time $t_2$.

The second and third inhalations in FIG. 4 are regulated in the same way as the first inhalation. The second and third inhalations are initiated at times $t_3$ and $t_5$ respectively, at which times the heater is again activated. The heater is initially controlled by a first control step or mode based on power regulation and, upon detection of a predetermined condition at times $t_{L2}$ and $t_{L3}$, resistances $R_2$ and $R_3$ are respectively recorded. Control of the heater then switches to a second control step or mode based on resistance regulation, which is used for the remainder of the inhalation until the second and third inhalations terminate at times $t_4$ and $t_6$ respectively.

The three separate recorded resistances $R_1$, $R_2$ and $R_3$ from the first three inhalations are used to determine a target resistance $R_T$, which is based on the average of the three recorded resistances $R_1$, $R_2$ and $R_3$. The fourth and fifth inhalations are regulated in the same way as the second and third inhalations of FIG. 3. The fourth and fifth inhalations in FIG. 4 are initiated at times $t_7$ and $t_9$ respectively, at which times the heater is again activated but is controlled by a second control step only based on resistance regulation until the inhalations terminate at times $t_8$ and $t_{10}$ respectively. The fourth and subsequent inhalations are regulated using the target resistance $R_T$ based on the average of the recorded resistances $R_1$, $R_2$ and $R_3$. This provides consistent aerosol generation for the fourth and subsequent inhalations.

Figure 5:
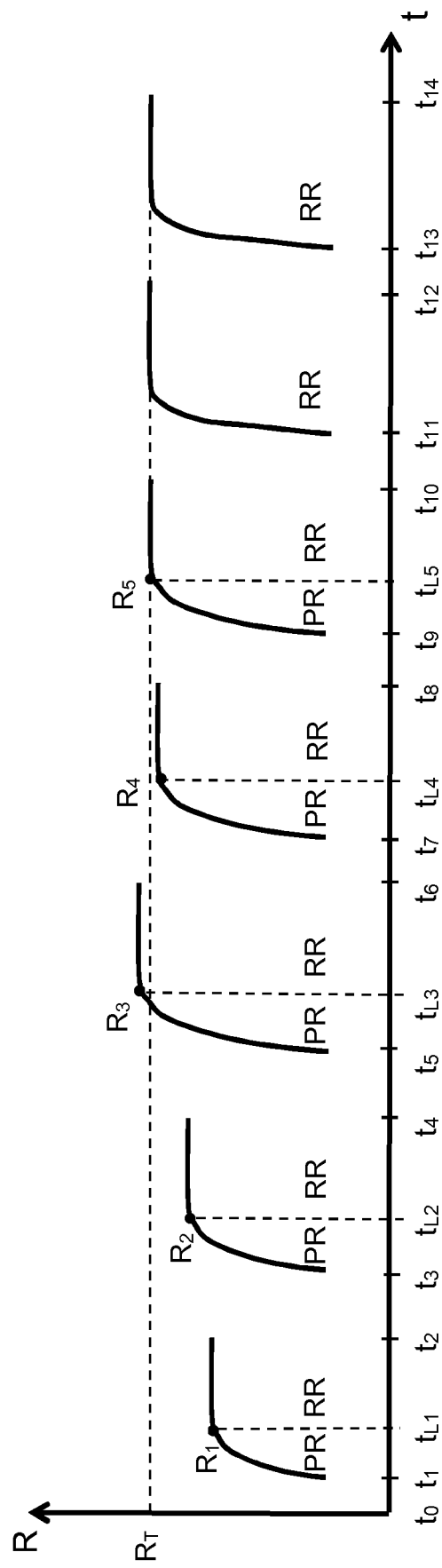
FIG. 5 is a schematic illustration of a temperature profile of a heater of an aerosol-generating system obtained by a method in accordance with another embodiment of the present invention.

FIG. 5 shows a graph of resistance R versus time t and the temperature profile of a heater of an aerosol-generating system which is heated by a method in accordance with another embodiment of the present invention. In particular, FIG. 5 shows the first seven inhalations or puffs of a user session in which the first five inhalations are regulated by hybrid regulation and the sixth and subsequent inhalations are regulated using resistance regulation only. This method may be used if the recorded resistance for the first few inhalations varies significantly, i.e. the variation in resistance is outside a predetermined or acceptable range, which may occur, for example, on initial start-up of the aerosol-generating system, before the system has thermally stabilised.

In FIG. 5, the system is enabled at time to and the user takes the first three inhalations or puffs at times $t_1$, $t_3$ and $t_5$ respectively, at which times the heater is activated. The first three inhalations of FIG. 5 are regulated in the same way as the first three inhalations in FIG. 4. During the first three inhalations, the heater is initially controlled by a first control step or mode based on power regulation. For each inhalation, a separate resistance, i.e. $R_1$, $R_2$ and $R_3$ respectively, is recorded upon detection of a predetermined condition for each inhalation at times $t_{L1}$, $t_{L2}$, and $t_{L3}$ respectively. At which points, control of the heater switches to a second control step or mode using resistance regulation based on the three respective recorded resistances, $R_1$, $R_2$ and $R_3$, which step or mode is used for the remainder of each of the inhalations until the inhalations terminate at time $t_2$, $t_4$ and $t_6$ respectively.

The condition to determine a target resistance may be that the recorded resistance for the last n number of inhalations or puffs falls within a maximum predetermined range $\Delta R_{max}$. If so, then the target resistance may be based on either the last recorded resistance or an average of the last n number of inhalations.

In FIG. 5, n is set to be 3 and the values of resistances $R_1$, $R_2$ and $R_3$ fall outside the maximum predetermined range $\Delta R_{max}$. In other words, the maximum value of $R_1$, $R_2$ and $R_3$ minus the minimum value of $R_1$, $R_2$ and $R_3$ is greater than the maximum predetermined range $\Delta R_{max}$, i.e. Max $\{R_1, R_2$ and $R_3\}$–Min $\{R_1, R_2$ and $R_3\} > \Delta R_{max}$. Accordingly, the method does not determine a target resistance but monitors a further inhalation taken by the user.

A fourth inhalation is taken at time $t_7$ and is regulated in the same way as the first three inhalations, i.e. using hybrid regulation. A fourth resistance $R_4$ is recorded upon detection of the predetermined condition at time $t_{L4}$ and the fourth inhalation terminates at time $t_8$. The method then examines the recorded resistances for the last three inhalations, i.e. $R_2$, $R_3$ and $R_4$. However, in FIG. 5, these three resistances also fall outside the maximum predetermined range $\Delta R_{max}$. Therefore the method does not determine a target resistance but monitors yet a further inhalation taken by the user.

A fifth inhalation is taken at time $t_9$ and is regulated in the same way as the first four inhalations, i.e. using hybrid regulation. A fifth resistance $R_5$ is recorded upon detection of the predetermined condition at time $t_{L5}$ and the fourth inhalation terminates at time $t_{10}$. The method then examines the recorded resistances for the last three inhalations, i.e. $R_3$, $R_4$ and $R_5$. In FIG. 5, these three resistances fall within the maximum predetermined range $\Delta R_{max}$ and therefore a target resistance $R_T$ can be determined. The target resistance $R_T$ can either be based on the last recorded resistance, i.e. $R_5$ or it can be based on an average of the recorded resistances of the last three inhalations, i.e. $R_3$, $R_4$ and $R_5$. In FIG. 5, the target resistance $R_T$ is based on the average of the recorded resistances of the last three inhalations, i.e. $R_3$, $R_4$ and $R_5$.

The sixth and seventh inhalations are regulated in the same way as the second and third inhalations of FIG. 3. The sixth and seventh inhalations in FIG. 5 are initiated at times $t_{11}$ and $t_{13}$ respectively, at which times the heater is again activated but is controlled by a second control step only based on resistance regulation until the inhalations terminate at times $t_{12}$ and $t_{14}$ respectively. The sixth and subsequent inhalations are regulated using the target resistance $R_T$ based on the average of the recorded resistances $R_3$, $R_4$ and $R_5$. This provides consistent aerosol generation for the sixth and subsequent inhalations.

Figure 6:
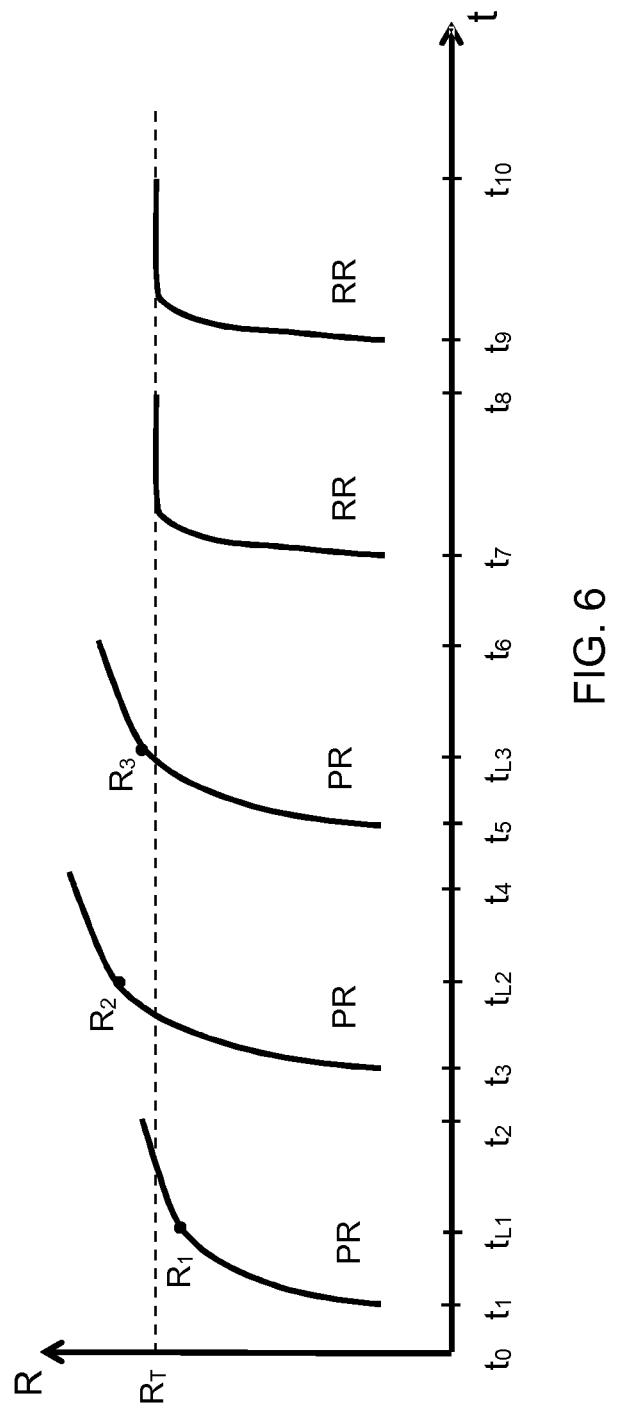
FIG. 6 is a schematic illustration of a temperature profile of a heater of an aerosol-generating system obtained by a method in accordance with another embodiment of the present invention.

FIG. 6 shows a graph of resistance R versus time t and the temperature profile of a heater of an aerosol-generating system which is heated by a method in accordance with another embodiment of the present invention. In particular, FIG. 6 shows the first five inhalations or puffs of a user session in which the first three inhalations are regulated by power regulation only and the sixth and subsequent inhalations are regulated using resistance regulation only.

The first three inhalations of FIG. 6 differ from the initial inhalations of the other examples shown in the figures in that they are regulated by power regulation only. In FIG. 6, the system is enabled at time $t_0$ and the user takes the first inhalation or puff at time $t_1$, at which time the heater is activated. During the inhalation, the heater is controlled by a first control step or mode only based on power regulation, in which a constant predetermined power corresponding to predetermined duty cycle is provided to the heater until the inhalation terminates at time $t_2$. Upon detection of a predetermined condition at time $t_{L1}$, a resistance $R_1$ is recorded. The predetermined condition in the example of FIG. 6 is the point at which the gradient of the temperature profile approaches zero.

As mentioned above, a power regulated system generally uses a relatively high predetermined power, for example, a duty cycle of 80% to 95%, in order to raise the temperature of the heater towards the target temperature as quickly as possible. Once the target temperature has been reached the power can be progressively decreased because it generally takes less power to maintain the heater at the target temperature than it does to heat it up. However, since the first inhalation does not switch to a second control step or mode during the inhalation, i.e. upon detection of the predetermined condition, the resistance is not regulated at the recorded resistance and therefore the temperature of the heater continues to increase above the recorded resistance, albeit at a lower rate.

A target resistance based on the recorded resistance $R_1$ could be determined upon detection of the predetermined condition, i.e. at time $t_{L1}$. For example, a target temperature could be determined if $R_1$ was within a predetermined range. However, the method shown in FIG. 6, takes an alternative approach and firstly monitors two further inhalations or puffs using power regulation alone before determining a target resistance in order to account for resistance variation in the first few inhalations.

The second and third inhalations in FIG. 6 are regulated in the same way as the first inhalation. The second and third inhalations are initiated at times $t_3$ and $t_5$ respectively, at which times the heater is again activated. The heater is controlled by a first control step or mode only based on power regulation only until the inhalations terminate at times $t_4$ and $t_6$ respectively. Upon detection of a predetermined condition at times $t_{L2}$ and $t_{L3}$, resistances $R_2$ and $R_3$ are respectively recorded.

The three recorded resistances $R_1$, $R_2$ and $R_3$ from the first three inhalations are used to determine a target resistance $R_T$, which is based on the average of the three recorded resistances $R_1$, $R_2$ and $R_3$. The fourth and fifth inhalations are regulated in the same way as the second and third inhalations of FIG. 3, i.e. using resistance regulation only. The fourth and fifth inhalations in FIG. 6 are initiated at times $t_7$ and $t_9$ respectively, at which times the heater is again activated but is controlled by a second control step only based on resistance regulation until the inhalations terminate at times $t_8$ and $t_{10}$ respectively. The fourth and subsequent inhalations are regulated using the target resistance $R_T$ based on the average of the recorded resistances $R_1$, $R_2$ and $R_3$. This provides consistent aerosol generation for the fourth and subsequent inhalations.

Alternatively, if the three recorded resistances $R_1$, $R_2$ and $R_3$ are not within a maximum predetermined range, the system can wait until the resistance stabilises and comes within the predetermined range before calculating a target resistance based on an average of the recorded resistances in a similar way to the method described in FIG. 5.

Figure 7:
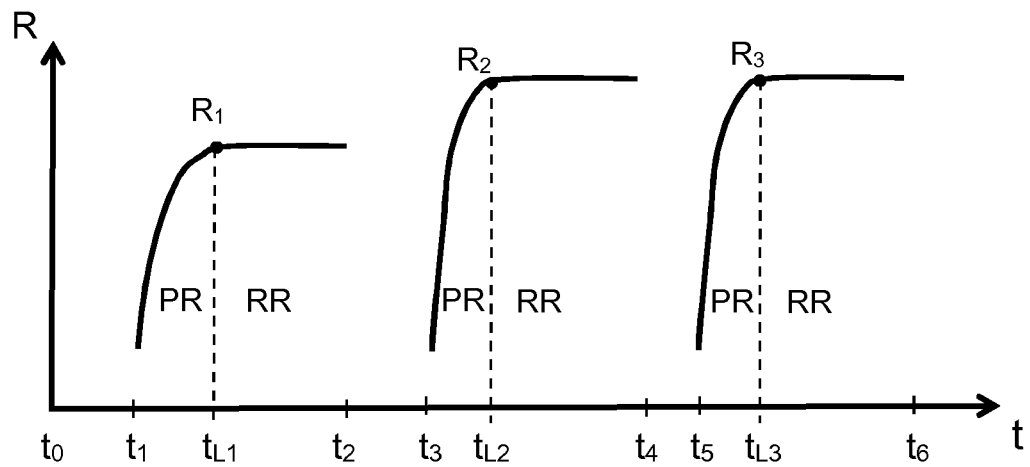
FIG. 7 is a schematic illustration of a temperature profile of a heater of an aerosol-generating system exhibiting a dry puff scenario.

FIG. 7 shows a graph of resistance R versus time t and the temperature profile of a heater of an aerosol-generating system in accordance with an embodiment of the present invention in which the heater is exhibiting a dry puff scenario. In particular, FIG. 7 shows the first three inhalations or puffs of a user session in which all inhalations are controlled by hybrid regulation, i.e. a combination of power regulation and resistance regulation. As discussed above, a "dry puff" or "dry heating" situation occurs when the heater is heated with insufficient liquid aerosol-forming substrate being present. This can result in overheating and, potentially, thermal decomposition of the liquid aerosol-forming substrate, which can produce undesirable by-products such as formaldehyde.

In FIG. 7, the system is enabled at time to and the user starts to take a first inhalation or puff at time $t_1$, which activates the heater. During the first inhalation, liquid is present at the heater, which is initially controlled by a first control step or mode based on power regulation. Upon detection of a predetermined condition at time $t_{L1}$, a resistance $R_1$ is recorded and a target resistance may be determined based on the recorded resistance $R_1$. At which point, control of the heater switches to a second control step or mode based on resistance regulation, which is used for the remainder of the inhalation until the inhalation terminates at time $t_2$.

The second and third inhalations of FIG. 7 are regulated in the same way as the first inhalation and are initiated at times $t_3$ and $t_5$ respectively. However, there is insufficient liquid aerosol-generating substrate available for the second and third inhalations and so dry puffs occur. Upon detection of a predetermined condition, a resistance $R_2$ is recorded at time $t_{L2}$ during the second inhalation and a resistance $R_3$ is recorded at time $t_{L3}$ during the third inhalation. Resistances $R_2$ and $R_3$ are markedly higher than resistance $R_1$ due to the dry puffs. This is because, in a power regulated system, a constant predetermined power is provided to the heater and, if insufficient liquid aerosol-forming substrate is present at the heater, for example, if the cartridge storing the liquid aerosol-forming substrate is empty, then there will be a marked increase in the ultimate temperature achieved and hence in the resistance recorded because less or no power is being expended in vaporising the liquid. Furthermore, the temperature will increase at a faster rate compared to when liquid is present, which is evident from the steeper rate of temperature increase for the second and third inhalations.

The system is configured to detect this marked increase in the recorded resistance due to there being insufficient liquid. In particular, the system is configured to detect when the recorded resistance increases above a threshold value. Upon detection, the system is able to isolate the heater to prevent further dry puffs, thereby reducing the likelihood of a user being exposed to undesired by-products. Instructions for detecting a dry puff and isolating the heater can be implemented in the software programmed into the controller.

Figure 8:
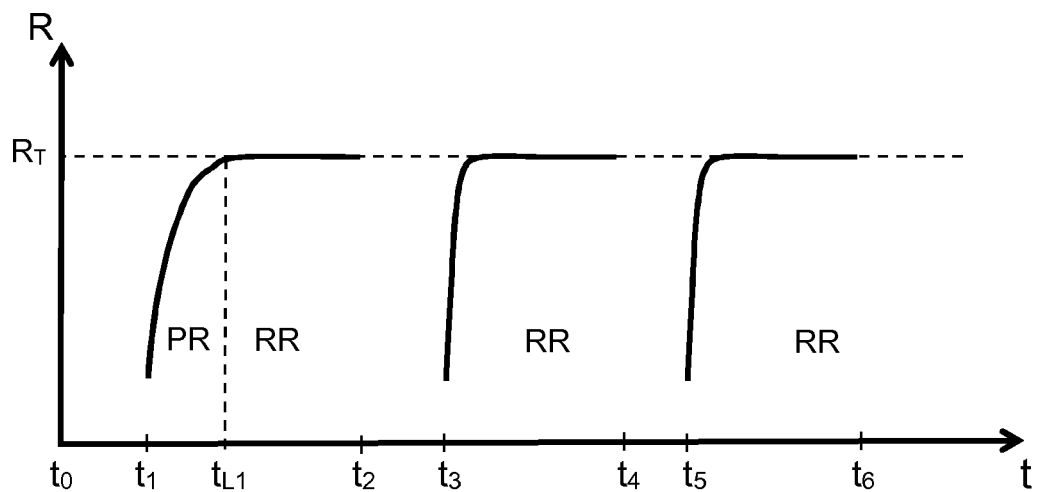
FIG. 8 is a schematic illustration of a temperature profile of a heater of an aerosol-generating system exhibiting another dry puff scenario.

FIG. 8 shows a graph of resistance R versus time t and the temperature profile of a heater of an aerosol-generating system in accordance with an embodiment of the present invention in which the heater is exhibiting another dry puff scenario. In particular, FIG. 8 shows the first three inhalations or puffs of a user session in which the first inhalation is regulated by hybrid regulation and subsequent inhalations are regulated by resistance regulation.

In FIG. 8, the system is enabled at time to and the user starts to take a first inhalation or puff at time $t_1$, which activates the heater. The first inhalation of FIG. 8 is regulated in the same way as the first inhalation in FIG. 7. During the first inhalation, liquid is present at the heater, which is initially controlled by a first control step or mode based on power regulation. Upon detection of a predetermined condition at time $t_{L1}$, a resistance is recorded and a target resistance $R_T$ is determined based on the recorded resistance. At which point, control of the heater switches to a second control step or mode based on resistance regulation, which is used for the remainder of the inhalation until the inhalation terminates at time $t_2$.

For the second and third inhalations there is insufficient liquid aerosol-generating substrate available at the heater and so dry puffs occur. The second and third inhalations in FIG. 8 are initiated at times $t_3$ and $t_5$ respectively, at which times the heater is again activated but is controlled by a second control step only based on resistance regulation in which the resistance is regulated to the target resistance $R_T$ of the first inhalation until the inhalations terminate at times $t_4$ and $t_6$ respectively. Since the system is adapting the power in the second and third inhalations to maintain a constant resistance, it is not possible to use a change in resistance to detect a dry puff scenario because it is being held constant. Instead, it is necessary to monitor the power required to maintain the target resistance and hence maintain the target temperature. When there is insufficient liquid aerosol-generating substrate at the heater, the power required to keep the temperature constant will be markedly lower than when liquid is present because power is not being expended in vaporising the liquid.

The system is configured to detect a marked reduction in the power required to maintain the heater at the target resistance. In particular, the system is configured to detect when the power required to maintain the heater at the target resistance decreases below a threshold value. Upon detection, the system is able to isolate the heater to prevent further dry puffs, thereby reducing the likelihood of a user being exposed to undesired by-products. Instructions for detecting a dry puff and isolating the heater can be implemented in the software programmed into the controller.

Figure 9:
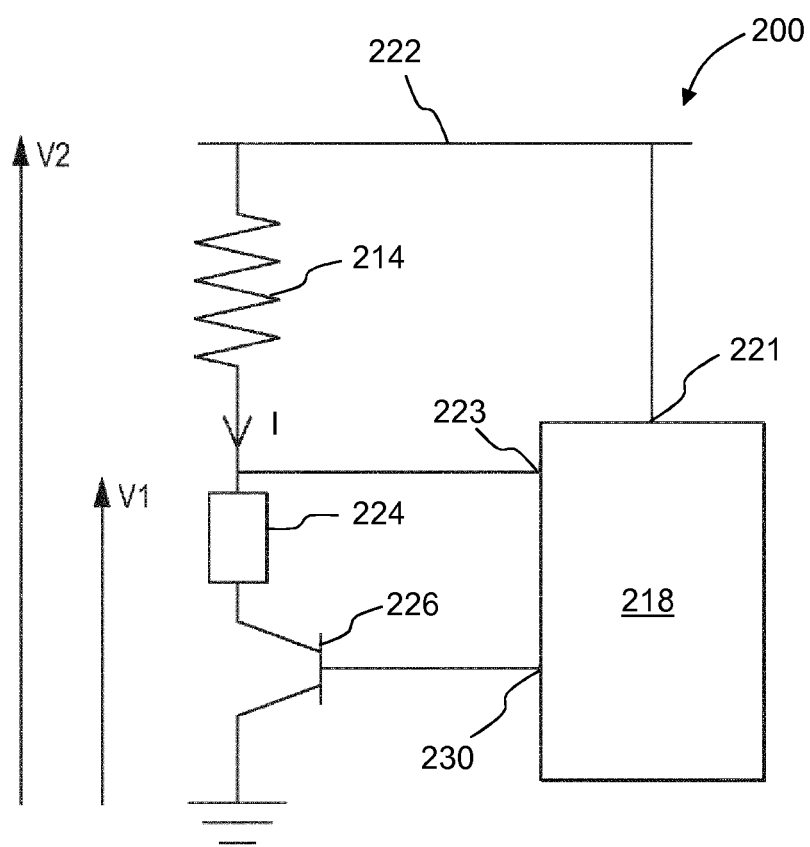
FIG. 9 is a schematic diagram of a temperature control circuit for an aerosol-generating system of the type shown in FIG. 1.

FIG. 9 illustrates control circuitry 200 used to provide the described temperature regulation in accordance with one embodiment of the invention.

The circuitry 200 includes a heater 214 comprising a resistive heating element, which is connected to an electric power supply via connection 222. The electric power supply provides a voltage V2. An additional resistor 224, with known resistance r, is inserted in series with the heater 214. There is a voltage V1 at the point in the circuit between the heater 214 and the additional resistor 224, i.e. at the ground side of the heater 214. The voltage V1 is intermediate between ground and voltage V2. Software for providing the temperature regulation is integrated into software programmed into a microcontroller 218, which is able to deliver a pulse width modulated voltage signal via an output 230 of the microcontroller 218 to a transistor 226 which acts as a simple switch for activating the heater 214 in accordance with the pulse width modulated voltage signal.

An indication of the temperature of the heater 214 (in this example the electrical resistance of the heater 214) is determined by measuring the electrical resistance of the heater 214. The indication of the temperature is used to adjust the duty cycle of the pulse width modulated voltage supplied to the heater 214 in order to maintain the heater close to a target resistance. The indication of the temperature is determined at a frequency chosen to match the timing required for the control process, and may be determined once every 100 ms or more frequently, as required.

An analog input 221 on the microcontroller 218 is used to monitor the voltage V2 at the electric power source side of the heater 214. An analog input 223 on the microcontroller is used to monitor the voltage V1 at the ground side of the heater 214.

The heater resistance to be measured at a particular temperature is $R_{heater}$. In order for microprocessor 218 to measure the resistance $R_{heater}$ of the heater 214, the current through the heater 214 and the voltage across the heater 214 can both be determined. Then, Ohm's law can be used to determine the resistance:

$$V = IR \quad (1)$$

In FIG. 9, the voltage across the heater is V2−V1 and the current through the heater is I. Thus:

$$R_{heater} = \frac{V2 - V1}{I} \quad (2)$$

The additional resistor 224, whose resistance r is known, is used to determine the current I, again using (1) above. The current through the resistor 224 is also I and the voltage across the resistor 224 is V1. Thus:

$$I = \frac{V1}{r} \quad (3)$$

So, combining (2) and (3) gives:

$$R_{heater} = \frac{(V2 - V1)}{V1} r \quad (4)$$

Thus, the microprocessor 218 can measure V2 and V1, as the aerosol generating system is being used and, knowing the value of r, can determine the heater's resistance $R_{heater}$ at a particular temperature.

The heater resistance $R_{heater}$ is correlated to temperature. A linear approximation can be used to determine the temperature T corresponding to the measured resistance $R_{heater}$ according to the following formula:

$$T = \frac{R_{heater}}{A R_0} + T_0 - \frac{1}{A} \quad (5)$$

where A is the thermal resistivity coefficient of the heater material and $R_0$ is the resistance of the heater at ambient temperature $T_0$.

An advantage of the control circuitry 200 is that no temperature sensor is required. Such sensors can be bulky and expensive. Also the resistance value can be used directly by the microcontroller instead of temperature. If the heater resistance $R_{heater}$ is held within a desired range, so too will the temperature of the heater 214. Accordingly, the actual temperature of the heater 214 does not need to be calculated during the control process, which improves computational efficiency. However, it is possible to use a separate temperature sensor and connect that to the microcontroller to provide the necessary temperature information, if desired.

The software programmed into the microcontroller 218 is configured to monitor for the predetermined condition and, upon detection of the predetermined condition, to record the resistance of the heater. The predetermined condition and the resistance can be stored in a memory of the microcontroller 218. The software programmed into the microcontroller 218 is configured to determine a target resistance based on the recorded resistance.

The microcontroller 218 is also configured to adapt the duty cycle of the pulse width modulated voltage signal to control the power provided to the heater in order to drive the resistance of the heater towards the target resistance such that the heater is driven towards a target temperature corresponding to the target resistance. To regulate the resistance, the heater resistance $R_{heater}$ is determined and an error between the determined heater resistance $R_{heater}$ and the target resistance is calculated. The duty cycle of the power is then adjusted using proportional-integral-derivative (PID) control to correct the error and drive the heater toward the target resistance. The PID control is integrated into the software programmed into the controller 218.

The power P provided to the heater 214 can be determined by the formula:

$$P = VI \quad (6)$$

where V is the voltage across the heater, i.e. V2−V1 and I is the current through the heater which can be determined using (3) above. The determined power can be used, for example, for detecting the dry puff scenario illustrated in FIG. 8.

The invention claimed is:

1. A method of controlling heating in an aerosol-generating system comprising a heater, the method comprising:
   a first control step in which a predetermined power is provided to the heater and a resistance of the heater is determined, wherein the determined resistance is indicative of a temperature of the heater;
   monitoring for a predetermined condition, and upon detection of the predetermined condition, recording a resistance of the heater;
   determining a target resistance corresponding to a target temperature of the heater based on the recorded resistance; and
   a second control step in which the predetermined power provided to the heater is controllably adapted to drive the resistance of the heater towards the target resistance such that the heater is driven towards the target temperature corresponding to the target resistance.

2. The method according to claim 1, wherein the method switches from the first control step to the second control step upon detection of the predetermined condition.

3. The method according to claim 1, wherein the predetermined condition is selected from one or more of the following:
an elapsed time from a start of a user inhalation,
a derivative of resistance being less than a predetermined threshold, and
a derivative of resistance being equal to zero.

4. The method according to claim 1, wherein the first control step and the second control step are performed during a user inhalation.

5. The method according to claim 1,
wherein the first control step and the second control step are performed during a first user inhalation, and
wherein a second and subsequent user inhalations use only the second control step.

6. The method according to claim 1, wherein the target resistance is determined following a plurality of initial user inhalations.

7. The method according to claim 1, wherein only the first control step and the step of monitoring for the predetermined condition, and upon the detection of the predetermined condition, recording the resistance of the heater are performed during a plurality of initial user inhalations.

8. The method according to claim 6, wherein the target resistance is determined based on an average of recorded resistances from the plurality of initial user inhalations.

9. The method according to claim 8,
wherein user inhalations following the plurality of initial user inhalations use only the second control step, and
wherein the target resistance is based on the average of the recorded resistances from the plurality of initial user inhalations.

10. A controller for an aerosol-generating system, the controller being configured to perform the method of claim 1.

11. A nontransitory computer-readable storage medium having a computer program stored thereon that when executed on electric circuitry of a programmable controller, causes the programmable controller to perform the method according to claim 1.

12. An aerosol-generating system, comprising:
a heater;
a power supply; and
a controller configured to:
provide a predetermined power to the heater and determine a resistance of the heater in a first control mode, wherein the determined resistance is indicative of a temperature of the heater,
monitor for a predetermined condition and upon detection of the predetermined condition, record a resistance of the heater,
determine a target resistance corresponding to a target temperature of the heater based on the recorded resistance, and
controllably adapt the power provided to the heater to drive the resistance of the heater towards the target resistance in a second control mode such that the heater is driven towards the target temperature corresponding to the target resistance.

13. The aerosol-generating system according to claim 12, wherein the controller is further configured to switch from the first control mode to the second control mode upon detection of the predetermined condition.

14. The aerosol-generating system according to claim 12, wherein the predetermined condition is selected from one or more of the following:
an elapsed time from a start of a user inhalation,
a derivative of resistance being less than a predetermined threshold, and
a derivative of resistance being equal to zero.

15. The aerosol-generating system according to claim 12, wherein the first control mode and the second control mode are used during a user inhalation.

16. The aerosol-generating system according to claim 12,
wherein the first control mode and the second control mode are used during a first user inhalation, and
wherein a second and subsequent user inhalations use only the second control mode.

17. The aerosol-generating system according to claim 12, wherein the target resistance is determined following a plurality of initial user inhalations.

18. The aerosol-generating system according to claim 12, wherein only the first control mode and the monitoring for the predetermined condition and upon detection of the predetermined condition, recording the resistance of the heater are used during a plurality of initial user inhalations.

19. The aerosol-generating system according to claim 17, wherein the target resistance is determined based on an average of the recorded resistances from the plurality of initial user inhalations.

20. The aerosol-generating system according to claim 19,
wherein user inhalations following the plurality of initial user inhalations use only the second control mode, and
wherein the target resistance is based on the average of the recorded resistances from the plurality of initial user inhalations.

* * * * *